United States Patent
Son et al.

(10) Patent No.: US 9,374,842 B2
(45) Date of Patent: Jun. 21, 2016

(54) PROXY COMMUNICATION SYSTEM AND PROXY COMMUNICATION SYSTEM CONTROLLING METHOD IN BAN ENVIRONMENT

(75) Inventors: Jae-Seung Son, Suwon-si (KR); Seung-Hoon Park, Seoul (KR); Tae-Han Bae, Seoul (KR); Eun-Tae Won, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 39 days.

(21) Appl. No.: 14/125,751

(22) PCT Filed: Jul. 4, 2012

(86) PCT No.: PCT/KR2012/005304
§ 371 (c)(1),
(2), (4) Date: Dec. 12, 2013

(87) PCT Pub. No.: WO2013/005985
PCT Pub. Date: Jan. 10, 2013

(65) Prior Publication Data
US 2014/0106673 A1    Apr. 17, 2014

(30) Foreign Application Priority Data
Jul. 5, 2011 (KR) .................. 10-2011-0066628

(51) Int. Cl.
*H04W 4/00* (2009.01)
*H04W 76/02* (2009.01)
(Continued)

(52) U.S. Cl.
CPC ........... *H04W 76/023* (2013.01); *A61B 5/0024* (2013.01); *H04B 13/005* (2013.01);
(Continued)

(58) Field of Classification Search
CPC .... H04W 4/005; H04W 4/008; H04W 76/023
USPC ..................... 340/539.12; 455/41.2
See application file for complete search history.

(56) References Cited

U.S. PATENT DOCUMENTS

2006/0174030 A1    8/2006  Choi et al.
2008/0320587 A1   12/2008  Vauclair et al.
(Continued)

FOREIGN PATENT DOCUMENTS

KR    10-2006-0088994 A    8/2006
KR    10-2007-0050057 A    5/2007
(Continued)

*Primary Examiner* — Ping Hsieh
(74) *Attorney, Agent, or Firm* — Jefferson IP Law, LLP (57) ABSTRACT

Disclosed is a method of controlling a communication system including one or more sensors attached to a user, a wireless communication apparatus, and a coordinator. The method of controlling the communication system includes receiving a request for a proxy authority for a proxy between the one or more sensors and the coordinator from the wireless communication apparatus and assigning the proxy authority to the wireless communication apparatus by the coordinator; generating a user identifier corresponding to the user by the wireless communication apparatus; searching for the one or more sensors attached to the user and establishing pairings with the found one or more sensors by the wireless communication apparatus; making a request for association information for an association between the coordinator and the sensors from the found one or more sensors and receiving the association information by the wireless communication apparatus; making a request for an association proxy for an association between the found one or more sensors and the coordinator from the coordinator and receiving the association proxy in response to the request by the wireless communication apparatus; and establishing an association with the found one or more sensors, making a request for data, and receiving the data in response to the request for the data by the coordinator.

18 Claims, 9 Drawing Sheets

(51) Int. Cl.
*A61B 5/00* (2006.01)
*H04B 13/00* (2006.01)
*H04L 29/08* (2006.01)
*H04L 29/06* (2006.01)
*H04W 12/06* (2009.01)
*H04W 8/00* (2009.01)
*H04L 12/58* (2006.01)
*G06F 19/00* (2011.01)

(52) U.S. Cl.
CPC ............ *H04L63/0884* (2013.01); *H04L 67/12* (2013.01); *H04L 67/28* (2013.01); *H04W 4/005* (2013.01); *H04W 12/06* (2013.01); *G06F 19/3418* (2013.01); *H04L 51/38* (2013.01); *H04W 4/008* (2013.01); *H04W 8/005* (2013.01)

(56) References Cited

U.S. PATENT DOCUMENTS

| | | |
|---|---|---|
| 2009/0011378 A1 | 1/2009 | Caminada |
| 2010/0315225 A1* | 12/2010 | Teague ..................... 340/539.12 |
| 2011/0025493 A1* | 2/2011 | Papadopoulos et al. . 340/539.12 |
| 2011/0221590 A1* | 9/2011 | Baker et al. .............. 340/539.12 |
| 2012/0202425 A1* | 8/2012 | Glezerman et al. .......... 455/41.2 |

FOREIGN PATENT DOCUMENTS

| | | |
|---|---|---|
| WO | 2010-100012 A1 | 9/2010 |
| WO | 2010-100443 A1 | 9/2010 |
| WO | 2010-100444 A1 | 9/2010 |

* cited by examiner

PROXY COMMUNICATION SYSTEM AND PROXY COMMUNICATION SYSTEM CONTROLLING METHOD IN BAN ENVIRONMENT

PRIORITY

This application is a National Phase Entry of PCT International Application No. PCT/KR2012/005304, filed on Jul. 4, 2012, and claimed the benefit of Korean Patent Application No. 10-2011-0066628, filed on Jul. 5, 2011, the contents of which are incorporated herein by reference.

TECHNICAL FIELD

The present invention relates to a proxy communication system and a proxy communication system controlling method in a BAN environment, and more particularly to a proxy communication system and a proxy communication system controlling method in a BAN environment where a medical or an entertainment service can be performed.

BACKGROUND ART

In recent times, researches on a communication system in connection with a medical field are being progressed. In general, the communication system related to the medical field mainly includes a sensor connected to a patient to detect a vital signal output from the patient and a coordinator connected to the sensor to collect data.

The patient wears one or more sensors on his/her body, and the one or more sensors detect different vital signals output from the patient and process data, respectively.

Meanwhile, the coordinator receives an input of data output from the one or more sensors, and can analyze the patient's overall health by gathering a plurality of data.

DISCLOSURE OF INVENTION

Technical Problem

However, sensors and coordinators in most communication systems related to the medical field are connected through a wire, and accordingly cause a cost problem in which one coordinator should be provided to one patient.

Further, the patient has a limitation in his/her movement since the sensor connected with the coordinator through the wire is attached to the patient's body, and a number of wired cables required for transmitting and receiving data is increased as a number of sensors attached to the patient is increased, so that a problem of intruding on the patient's convenience is generated.

Meanwhile, the discuss on standards for operating a medical or an entertainment service such as IEEE 802.15.4 Zigbee or IEEE 802.15.6 Body Area Network (hereinafter, referred to as BAN) are being progressed, and it is required to develop a wireless communication system between a sensor and a coordinator using a frequency band of the standard.

Solution to Problem

Accordingly, an aspect of the present invention is to solve the above-mentioned problems occurring in the prior art, and the present invention provides a communication system including a proxy apparatus capable of wirelessly transmitting and receiving data between the coordinator and the sensor in the BAN environment.

In accordance with a first aspect of the present invention, there is provided a method of controlling a communication system including one or more sensors attached to a user, a wireless communication apparatus, and a coordinator, the method including receiving a request for a proxy authority for a proxy between the one or more sensors and the coordinator from the wireless communication apparatus and assigning the proxy authority to the wireless communication apparatus by the coordinator; generating a user identifier corresponding to the user by the wireless communication apparatus; searching for the one or more sensors attached to the user and establishing pairings with the found one or more sensors by the wireless communication apparatus; making a request for association information for an association between the coordinator and the sensors from the found one or more sensors and receiving the association information by the wireless communication apparatus; making a request for an association proxy for an association between the found one or more sensors and the coordinator from the coordinator and receiving the association proxy in response to the request by the wireless communication apparatus; and establishing an association with the found one or more sensors, making a request for data, and receiving the data in response to the request for the data by the coordinator.

In accordance with a second aspect of the present invention, there is provided a communication system including one or more sensors attached to a user, a wireless communication apparatus, and a coordinator, the coordinator including a first communication unit for receiving proxy authority request data for a proxy between the one or more sensors and the coordinator from the wireless communication apparatus and a first controller for controlling such that the first communication unit transmits a proxy authority in response to the proxy authority request data.

Meanwhile, the wireless communication apparatus may include a second communication unit for receiving the proxy authority and a second controller for generating a user identifier corresponding to and the user, searching for the one or more sensors attached to the user, and controlling such that the second communication unit establishes a pairing with the found one or more sensors.

Further, the one or more sensors may include a third communication unit for receiving a request for association information for an association between the coordinator and the sensors from the wireless communication apparatus and a third controller for controlling such that the third communication unit transmits the association information to the wireless communication apparatus in response to the request.

Here, the second controller controls such that the second communication unit makes a request for an association proxy between the found one or more sensors and the coordinator from the coordinator, and the second communication unit can receive the association proxy in response to the request.

Further, the first controller controls such that first communication unit makes a request for data by establishing an association with the found one or more sensors, and the third controller can control such that the third communication unit transmits the data in response to the request for the data.

Advantageous Effects of Invention

According to various embodiments of the present invention, data transmission/reception between the coordinator and the sensor can be wirelessly implemented and accordingly it is possible to generate an effect of maximizing the patient's convenience.

Further, the coordinator assigns an authority allowing to perform some or all of functions of the coordinator to the wireless communication apparatus for playing a role as a medium enabling the data transmission/reception between the coordinator and the sensor. Accordingly, The wireless communication apparatus receiving the authority from the coordinator acts as the proxy.

Therefore, vital signal data of all patients can be easily transmitted to the coordinator through an approach to the patients by a manager carrying the proxy apparatus such as a nurse who checks the patient's health.

Also, one central coordinator can receive the vital signal data from an individual sensor of each patient through the proxy apparatus without a plurality of coordinator corresponding to a number of patients, so that costs required for providing the coordinator can be reduced.

MODE FOR THE INVENTION

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear.

Figure 1:
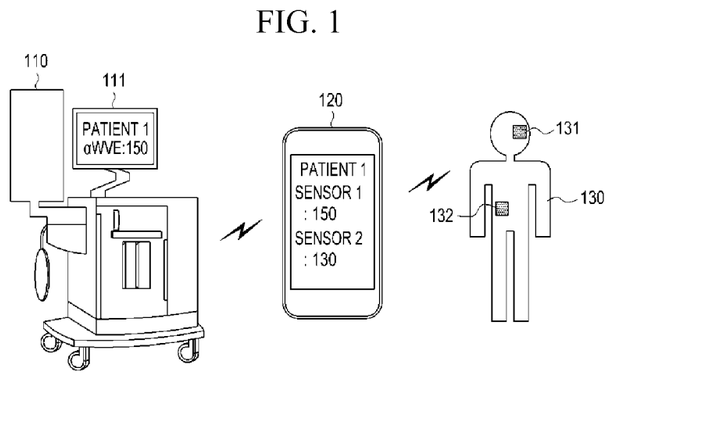
FIG. 1 illustrates a concept for describing a communication system in a BAN environment according to embodiments of the present invention.

FIG. 1 illustrates a concept for describing a communication system in a BAN environment according to embodiments of the present invention.

As shown in FIG. 1, the communication system in the BAN environment may include a coordinator 110, a wireless communication apparatus 120, and one or more sensors 131 and 132.

The coordinator 110 receives data and the like related to a vital signal output from the one or more sensors 131 and 132 and processes the input data based on a preset algorithm, program, or application. Further, the coordinator 110 can output a result of the processed data through a display means 111 and the like. Alternatively, the coordinator 110 can store the input data, and can display the stored data or output to other devices according to a user's control.

The coordinator 110 can wirelessly perform communication with the wireless communication apparatus 120 which is a proxy apparatus as shown in FIG. 1. The coordinator 110 can perform the communication with the wireless communication apparatus 120 by using various types of known communication technologies such as a general cellular communication scheme, a Wi-Fi (Wireless-Fidelity) communication scheme, a Blue-tooth communication scheme, a NFC (Near Field Communication) scheme and the like.

Meanwhile, the coordinator 110 can perform communication directly with the one or more sensors 131 and 132, and it is preferable that the coordinator 110 performs the communication with the one or more sensors 131 and 132 by using a short-distance communication scheme such as the NFC communication scheme or the BAN communication scheme. Communication implemented between the coordinator 110 and the wireless communication apparatus 120 or between the coordinator 110 and the sensors 131 and 132 may include various types of communication depending on the application by those skilled in the art.

The wireless communication apparatus 120 may be a kind of proxy apparatus and can act for pairings between the sensors 131 and 132 and the coordinator 110.

More specifically, the wireless communication apparatus 120 can make a request for a proxy authority for a proxy between the one or more sensors 131 and 132 and the coordinator from the coordinator 110 and can be assigned the proxy authority by the coordinator 110.

Thereafter, the wireless communication apparatus 120 can generate a user identifier corresponding to a user wearing the sensors 131 and 132 and store information on the generated user identifier. The wireless communication apparatus 120 can search for the one or more sensors 131 and 132 attached to the user based on the assigned proxy authority.

The wireless communication apparatus 120 broadcasts an inquiry packet based on a preset communication scheme, for example, an NFC scheme and the like, and can search for and find sensors adjacent to the wireless communication apparatus 120 by receiving a response packet transmitted from the sensors 131 and 132 in response to the inquiry packet. Here, the inquiry packet broadcasted by the wireless communication apparatus 120 may be defined based on a communication scheme set between the wireless communication apparatus 120 and the sensors 131 and 132, and it is easily understood by those skilled in the art that the inquiry packet may be variously modified according to a type of the set communication scheme.

The wireless communication apparatus 120 can establish a pairing with each of the found sensors 131 and 132. Here, types of communication schemes between the wireless communication apparatus 120 and respective sensors 131 and 132 may be the same or different. When the types of communication schemes between the wireless communication apparatus 120 and the respective sensors 131 and 132 are the same, the wireless communication apparatus 120 first establishes the pairing with one sensor in a time series and then establishes the pairing with the other sensor. When the types of communication schemes between the wireless communication apparatus 120 and the respective sensors 131 and 132 are different, the wireless communication apparatus 120 can independently establish the pairings with the respective sensors 131 and 132 at the same time.

Meanwhile, the wireless communication apparatus 120 can establish the pairings with all of the found sensors or some of the found sensors according to a user's selection.

The wireless communication apparatus 120 can establish the pairing with the sensors 131 and 132 in the aforementioned way. When the pairing is established, the wireless communication apparatus 120 can make a request for association information for an association between the coordinator 110 and each of the sensors 131 and 132 sequentially or simultaneously, and receive corresponding association information from each of the sensors 131 and 132. Here, the association information may contain information on the respective sensors 131 and 132 or information on the user identifier received from the wireless communication apparatus 120, and a detailed description of the association information will be discussed later.

Thereafter, the wireless communication apparatus 120 can make a request for association proxy for an association between one the found one or more sensors 131 and 132 and the coordinator 110 from the coordinator 110, and receive the association proxy in response to the request. Here, the association proxy may contain an identifier of the wireless communication apparatus 120, the user identifier, the information on the respective sensors 131 and 132 and the like, and the association proxy will be described later in detail.

The sensors 131 and 132 can be attached to a user's body to receive a vital signal output from the user's body. The sensors 131 and 132 can process the received vital signal so that the vital signal has a data form in which communication can be performed, and transmit/receive the processed data to/from the coordinator 110 or the wireless communication apparatus 120.

As described above, the sensors 131 and 132 can establish the pairing with the wireless communication apparatus 120 and transmit the association information according to the request of the wireless communication apparatus 120.

Further, the sensors 131 and 132 can receive an association response informing that the association between the sensors 131 and 132 and the coordinator 110 has been established from the coordinator 110. Furthermore, the sensors 131 and 132 can receive a data transmission request from the coordinator 110 and transmit data in response to the received data transmission request to the coordinator 110.

As described above, the coordinator 110 can wirelessly perform the communication with the wireless communication apparatus 120 or each of the sensors 131 and 132. Particularly, the proxy apparatus such as the wireless communication apparatus 120 can intervene in the communication system, and accordingly it is possible to more efficiently and stably manage the data.

Hereinafter, an operation related to various embodiments of the communication system in the BAN environment will be described in more detail based on a timing diagram.

Figure 2:
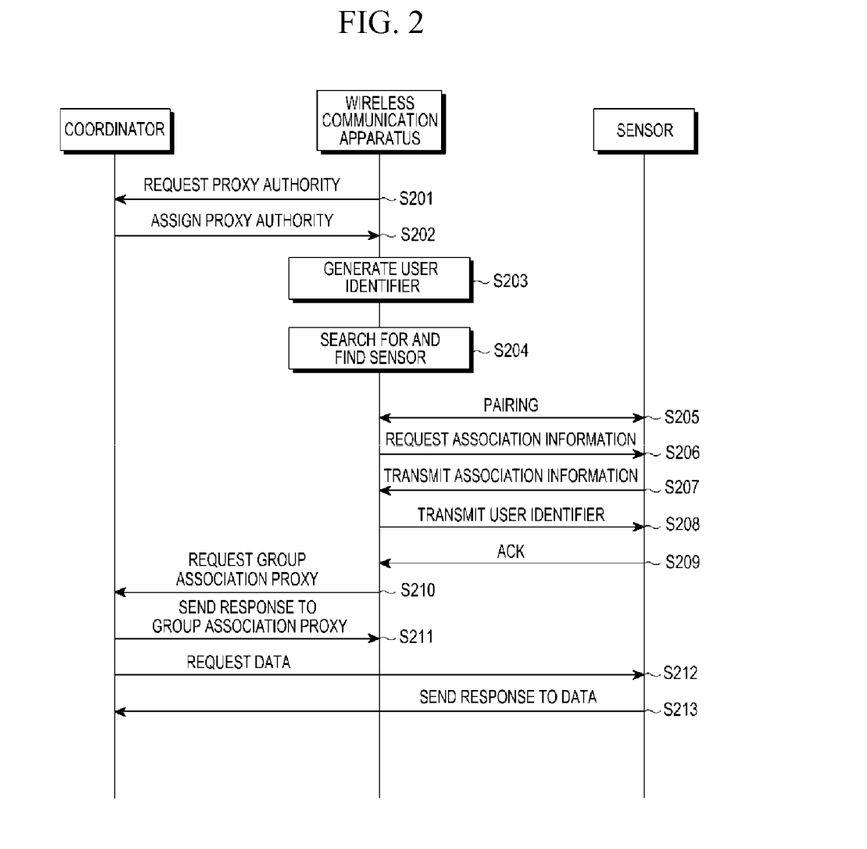
FIG. 2 is a timing diagram illustrating a method of controlling a communication system according to an embodiment of the present invention.

FIG. 2 is a timing diagram illustrating a method of controlling a communication system according to an embodiment of the present invention. The communication system of FIG. 2 includes the coordinator and the wireless communication apparatus, and it is assumed in embodiments of FIG. 2 that the wireless communication apparatus searches for and find one sensor.

As shown in FIG. 2, the wireless communication apparatus can make a request for a proxy authority from the coordinator in step S201. Here, the proxy authority may be an authority which allows the wireless communication apparatus to perform some or all of functions of the coordinator. For example, the wireless communication apparatus assigned the authority can perform an operation of connecting the coordinator and the sensors, and data fields and the like related thereto will be described later in more detail.

The coordinator can assign the proxy authority to the wireless communication apparatus in response to the received request for the proxy authority in step S202.

The wireless communication apparatus can generate the user identifier first corresponding to the user wearing the sensor based on the assigned proxy authority in step S203. The user identifier can be used for providing information on the user wearing each sensor.

Here, the wireless communication apparatus can generate the user identifier based on an external input. Alternatively, the wireless communication apparatus can generate the user identifier based on an RFID tag related to user information located in the surroundings of the user or an RF signal received from an RF signal generating apparatus. Meanwhile, it can be easily understood by those skilled in the art that the wireless communication apparatus can generate the user identifier by using various methods other than the above mentioned methods, and the methods of generating the user identifier do not limit a process of generating the user identifier.

The wireless communication apparatus can search for and find sensors located in the surroundings of the wireless communication apparatus in step S204. The wireless communication apparatus can broadcast an inquiry packet to search for sensors located in the surroundings of the wireless communication apparatus as described above, and can find sensors located in the surroundings of the wireless communication apparatus by identifying a response packet received in response to the inquiry packet. It is preferable that the wireless communication apparatus searches for the sensors based on a super-proximity communication scheme such as the NFC scheme.

The wireless communication apparatus can establish pairings for the found sensors in step S205. Here, the wireless communication apparatus can establish the pairings for all of the found sensors or some of the found sensors based on an external signal input by a selection of the sensor.

The wireless communication apparatus can make a request for association information for an association with the coordinator and the sensors from the sensors in step S206. Here, the association information may contain an MAC header, information on the sensors and the like, and data fields related thereto will be described later in more detail.

Meanwhile, the sensor, for example, may include a communication module such as an IEEE 802.15.4 Zigbee communication module. The sensor can shift the communication module from a disabled state to an enabled state when the sensor receives an association information request signal. The communication module may be in a standby state before receiving a data request from the coordinator.

The sensor can transmit association information in response to the received request for the association information in step S207.

When receiving the association information from the sensor in step 207, the wireless communication apparatus can transmit the generated user identifier to the sensor in step S208. The sensor can store the received user identifier in a storage medium included in the sensor. The sensor having received the user identifier can transmit an acknowledgement message (response message) to the wireless communication apparatus in step S209.

Meanwhile, when the sensor does not include a particular separate storage medium, the step in which the wireless communication apparatus transmits the user identifier may be omitted. After storing the user identifier, the sensor can transmit information on the user identifier when transmitting data to the coordinator in the future, and accordingly the coordinator can easily analyze a position of the sensor attached to the user.

The wireless communication apparatus can make a request for association proxy for an association between the coordinator and the sensor from the coordinator in step S210. Meanwhile, although FIG. 2 illustrates the pairing between the wireless communication wireless and one sensor, the pairing can be established between the wireless communication apparatus and two or more sensors. In this case, group association proxy can be requested in step S210. Here, the association proxy may contain an identifier of the wireless communication apparatus, the user identifier, information on the sensor and the like, and data fields of the association proxy and a more detailed description will be described later.

The coordinator can transmit a response to the association proxy to the wireless communication apparatus in step S211. The coordinator receives the request for the association proxy and can transmit a response to the request for the association proxy, so that the association between the coordinator and the sensor can be established.

The coordinator can make a request for predetermined data from the sensor in step S212. Here, the data may be a vital signal collected by the sensor from a user's body or data processed in a preset manner, and the data and related data fields will be described later in more detail.

The sensor can transmit data in response to the request for the predetermined data to the coordinator in step S213. Alternatively, although the coordinator does not make a request for data transmission, the sensor can transmit periodically monitored information to the coordinator.

As described above, the wireless communication apparatus can be implemented as the proxy apparatus acting for the pairing for the found sensors, and accordingly each user can easily and efficiently process the data collected from the sensor attached to the user.

Figure 3A:
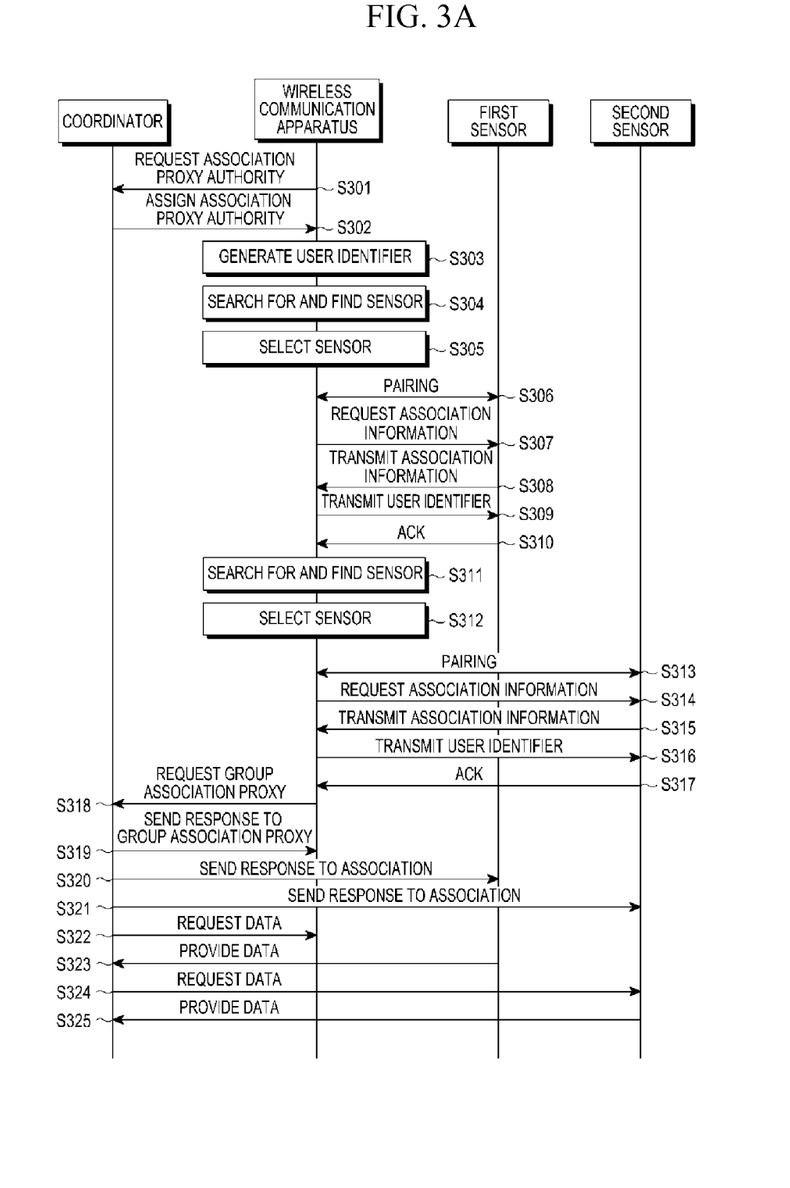
FIG. 3A is a timing diagram related to a method of controlling a communication system according to another embodiment of the present invention.

FIG. 3A is a timing diagram related to a method of controlling a communication system according to another embodiment of the present invention. Meanwhile, a description of the same construction as that related to the method of controlling the communication system of FIG. 2 will be omitted or briefly discussed.

The wireless communication apparatus can make a request for an association proxy authority from the coordinator in step S301, and the coordinator can assign the association proxy authority in response to the request in step S302.

Figure 3B:
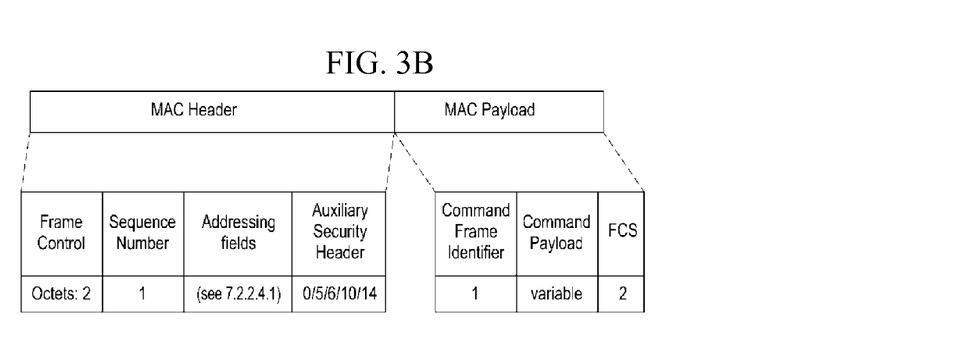
FIGS. 3B to 3I illustrate frame formats according to various embodiments of the present invention.

FIG. 3B illustrates an association proxy authority command frame format. As shown in FIG. 3B, an association proxy authority command frame may include an MAC header (hereinafter, referred to as an MHR) and an MAC payload. Here, the MHR is a header and includes a frame control field, a sequence number field, an addressing filed, an auxiliary security header, and the MAC payload includes a command frame identifier, command frame related information, etc. The command frame identifier includes an association proxy authority request identifier or an association proxy authority response identifier.

The frame control field indicates information on a frame type, use or non-use of a security, a frame version and the like. The sequence number field indicates a transmission order, and the addressing field indicates a PAN (Personal Area Network) ID of a transmitting/receiving device and an address of the device. The auxiliary security field indicates a method by which the frame is secured.

Meanwhile, in steps S301, S401, S501, S601, and S701 in which the wireless communication apparatus makes a request for the association proxy authority from the coordinator, the wireless communication apparatus can transmit the association proxy authority request and additionally transmit the identifier of the wireless communication apparatus. The identifier of the wireless communication apparatus may be included in a source address field (not shown) within the addressing field of the MHR field of FIG. 3 and then transmitted.

Meanwhile, the coordinator can store the identifier of the wireless communication apparatus received from the wireless communication apparatus and assign the proxy authority to the wireless communication apparatus by transmitting an authorization in steps S302, S402, S502, S602, and S702.

Figure 3C:
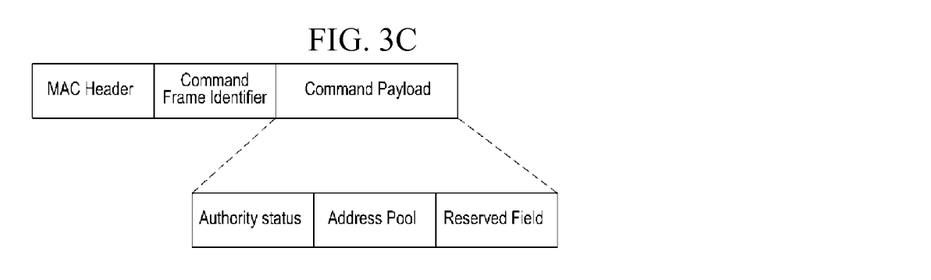

FIG. 3C illustrates a message construction when the association proxy authority frame is operated including an association proxy authorization identifier according to embodiments of the present invention. In this case, an authority status indicates a result of a response to the proxy authority request, and an address pool indicates address information which the wireless communication apparatus transmits to the sensor. A reserved field is allocated for the additional use in the future.

Meanwhile, the association proxy authority request identifier can be transmitted using a frame format defined in IEEE 802.15.4. The frame format defined in IEEE 802.15.4 includes an association request command field and an association proxy authority request field.

Figure 3D:
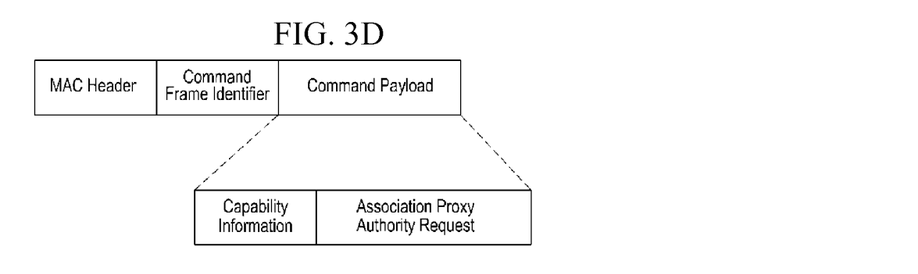

Specifically, as shown in FIG. 3D, the association request command field includes an MHR field, a command frame identifier, and capability information, and an association proxy request identifier can be transmitted after being inserted in the association proxy authority request field.

After receiving the association proxy authority, the wireless communication apparatus can generate the user identifier in step S303, and can search for and find sensors located in the surroundings of the wireless communication apparatus in step S304. It is assumed in an embodiment of FIG. 3A that two sensors including a first sensor and a second sensor are found.

Meanwhile, the wireless communication apparatus can additionally find a sensor other than the first and second sensors. When it is determined that the additionally found sensor is not attached to a corresponding user, a manager can exclude the additionally found sensor from a pairing process by inputting an external signal to an interface and the like in step S305. Meanwhile, the wireless communication can determine that a sensor of which a signal intensity is smaller than a preset value is not attached to the corresponding user based on an intensity of a signal received from each sensor and exclude the sensor from the pairing process. Also, it is easily understood by those skilled in the art that other examples which can be variously modified can be applied to the present invention.

The wireless communication apparatus can sequentially perform the pairing operation and the association operation for the two found sensors. For example, the wireless communication apparatus first establishes the pairing with the first sensor and then the pairing with the second sensor. Here, the pairing with the first sensor and the pairing with the second sensor can be performed based on the same communication standard or different communication standards. Meanwhile, when the two pairings are established based on different communication standards, the two pairings can be independently established at the same time.

The wireless communication apparatus makes a request for association information for the association operation from the first sensor in step S306. The wireless communication apparatus can make the request for the association information by transmitting an association information request frame to the first sensor. Meanwhile, the wireless communication apparatus can additionally transmit information on the coordinator, for example, information on a channel and the like used by the coordinator simultaneously in making the request for the association information. The wireless communication apparatus can select one address from the address pool received in step S302 in which the wireless communication apparatus receives the authority, and transmit the selected one address.

Figure 3E:
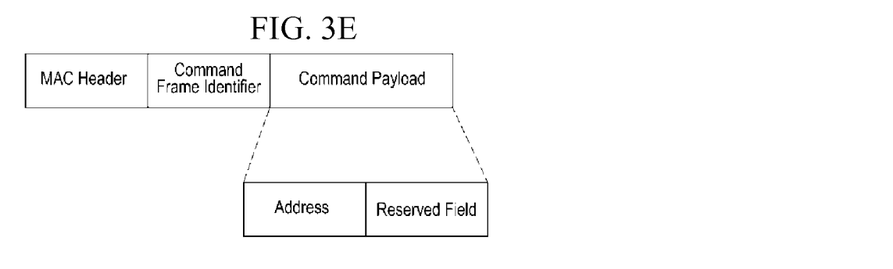

FIG. 3E illustrates a concept of a frame format of the association information request message (in steps S307, S314, S407, S412, S506, S510, S606, S617, S707, and S717). As shown in FIG. 3E, the association request message may include an MHR field, a command frame identifier, an address, and a reserved field.

Here, the MHR field is an MAC header and has a form of contents copied from the MHR field received from the coordinator. The command frame identifier indicates an MAC command type, and refers to an identifier herein indicating the association information request message. The address refers to an address which can be used by the sensor performing communication with the coordinator. The reserved field may be a part allocated for the use in the future.

The first sensor can transmit the association information to the wireless communication apparatus in response to the request for the association information in step S308. After transmitting the association information to the wireless communication apparatus, the first sensor makes the communication module be in an enabled state and thus can standby until finally receiving the association response from the coordinator. The first sensor can be set to wait for receiving the association response during a preset time, and the set preset time can be set to be longer than a general association standby time in consideration of a manager's action.

The first sensor can transmit the association information to the wireless communication apparatus by transmitting the association information response frame. Here, the association information response frame may include a sensor identifier (device ID) and sensor information (device information).

Figure 3F:
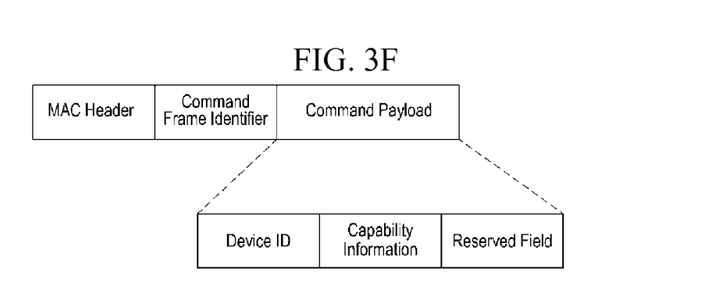

FIG. 3F illustrates a data frame format of the association information response message (in steps S308, S408, S413, S507, S511, S607, S618, S708, and S718) according to embodiments of the present invention. As shown in FIG. 3F, the association information response message may include an MHR field, a command frame identifier, a sensor identifier (device ID), capability information, and a reserved field.

Here, the MHR field is a header, and the command frame identifier indicates an MAC command type and refers to an identifier indicating the association information response message herein. The sensor identifier may be a sensor identifier of the first sensor transmitted to the coordinator.

Additionally, the capability information may be, for example, information on a serial number, a type, a battery type and the like. With regard to the capability information, when the coordinator includes an information database for an individual sensor, the capability information may contain only information for a sensor identification such as the serial number and the like. When the coordinator does not include the information database for the individual sensor, the capability information may contain the serial number, the type, and the battery type as described above. The reserved field may be allocated for the use in the future.

Figure 3G:
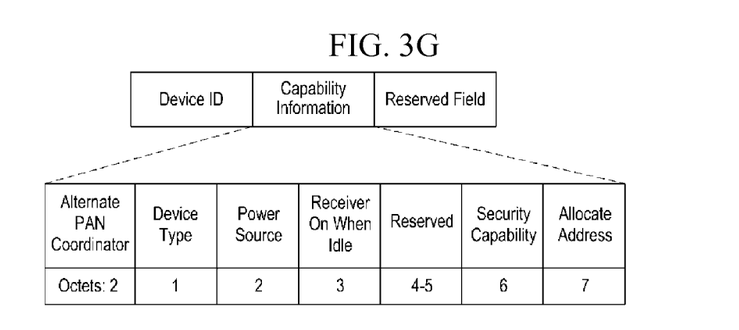

FIG. 3G illustrates a capability information field format of IEEE 802.15.4 as a comparison example of the present invention. As shown in FIG. 3G, the capability information may indicate a device type, use or non-use of a battery (power source) and the like.

When receiving the association information from the first sensor in step S308, the wireless communication apparatus can transmit the generated user identifier to the first sensor in step S309. Here, it is assumed that the first sensor includes a storage medium for storing the user identifier.

The first sensor informs the wireless communication apparatus whether the first sensor has received the user identifier by transmitting an acknowledgement frame to the wireless communication apparatus in step S310.

The wireless communication apparatus can repeat the pairing operation and the association operation with the second sensor in the same way as those with the first sensor in steps S311 to S317.

The wireless communication apparatus can make a request for the association proxy for the association between the first and second sensors and the coordinator from the coordinator in step S318. Here, as the wireless communication apparatus makes the request for the association proxy for two sensors, the association proxy may be referred to as group association proxy.

As the wireless communication apparatus transmits a group association proxy request command frame to the coordinator, the group association proxy can be transmitted to the coordinator. The group association proxy may include at least one of the wireless communication apparatus identifier, the user identifier, a sensor identifier list, and a capability information list.

Figure 3H:
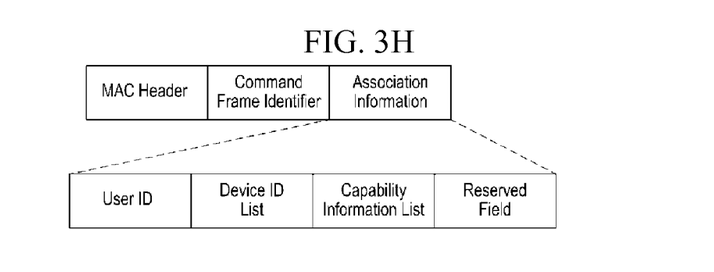

FIG. 3H illustrates a data frame format of the group association proxy request message (steps in S318, S416, S512, S610, S621, S709, and S719) according to embodiments of the present invention. As shown in FIG. 3H, the group association proxy request message may include an MHR field, a command frame identifier, and association information. Here, the MHR field is an MAC header, and information on the wireless communication apparatus is transmitted to a source address field.

The command frame identifier indicates an MAC command type, and includes a group association request identifier herein. The association information is a part of the MAC command, and may include a user identifier (user ID), a sensor identifier list (device ID list), a capability information list, and a reserved field. The sensor identifier list is a list of paired sensors. Additionally, the capability information list includes additional information on respective sensors (e.g. a device type), and use or non-use of a battery (power source).

The coordinator can transmit a group association proxy response in response to the group association proxy request from the wireless communication apparatus in step S319. The coordinator can transmit the group association proxy response by transmitting a group association proxy response command frame.

Figure 3I:
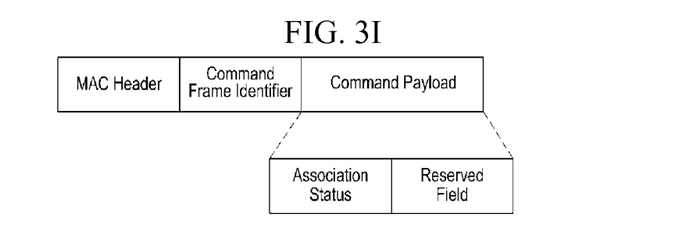

FIG. 3I illustrates a group association proxy response message (in steps S319, S417, S513, S611, S622, S710, and S720) according to embodiments of the present invention. As shown in FIG. 3I, a group association proxy response command frame may include an MHR field, a command frame identifier, an association status, and a reserved field.

Here, the MHR field is an MAC header, and the command frame identifier indicates a type of the MAC command and includes a group association proxy response identifier herein. The association status indicates a result of the response to the association request, and the reserved field can be allocated for the use in the future.

The coordinator can transmit the association response to both the first sensor and the second sensor in steps S320 and S321. When the first and second sensors receive the association response from the coordinator, each sensor can determine that the association has been completed and accordingly each sensor can transmit data in response to a data request (in steps S322 and S324) from the coordinator in steps S323 and S325. Alternatively, although the coordinator does not make the request for the data transmission, the sensor can transmit periodically monitored information to the coordinator.

Figure 4:
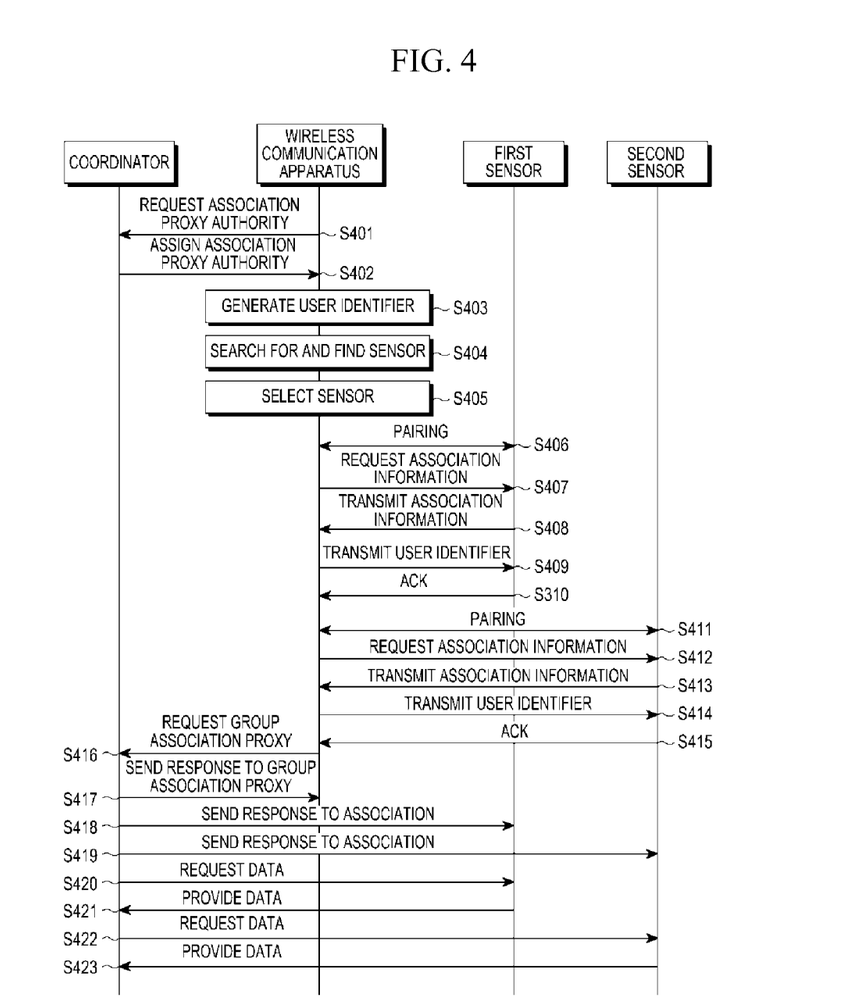
FIG. 4 is a timing diagram related to a method of controlling a communication system according to another embodiment of the present invention.

FIG. 4 is a timing diagram related to a method of controlling a communication system according to another embodiment of the present invention. The method of controlling the communication system according to FIG. 4 is similar to the method of controlling the communication system according to FIG. 3A. However, the method of controlling the communication system of FIG. 4 is different from the method of controlling the communication system of FIG. 3A in that the wireless communication apparatus performs the step S405 of first selecting the sensor only one time by searching for and finding the sensor in step S404.

The method of controlling the communication system of FIG. 3A performs the step of searching for and finding the first and second sensors two times in steps S304 and S311. In contrast, the method of controlling the communication system of FIG. 4 can find the first and second sensors by performing the step of searching for and finding the sensor only one time in step S404.

Other steps S401 to S403 and S406 to S423 of FIG. 4 can be implemented in the same way as those of FIG. 3A, and accordingly detailed descriptions of steps S401 to S403 and S406 to S423 will be omitted herein.

Figure 5:
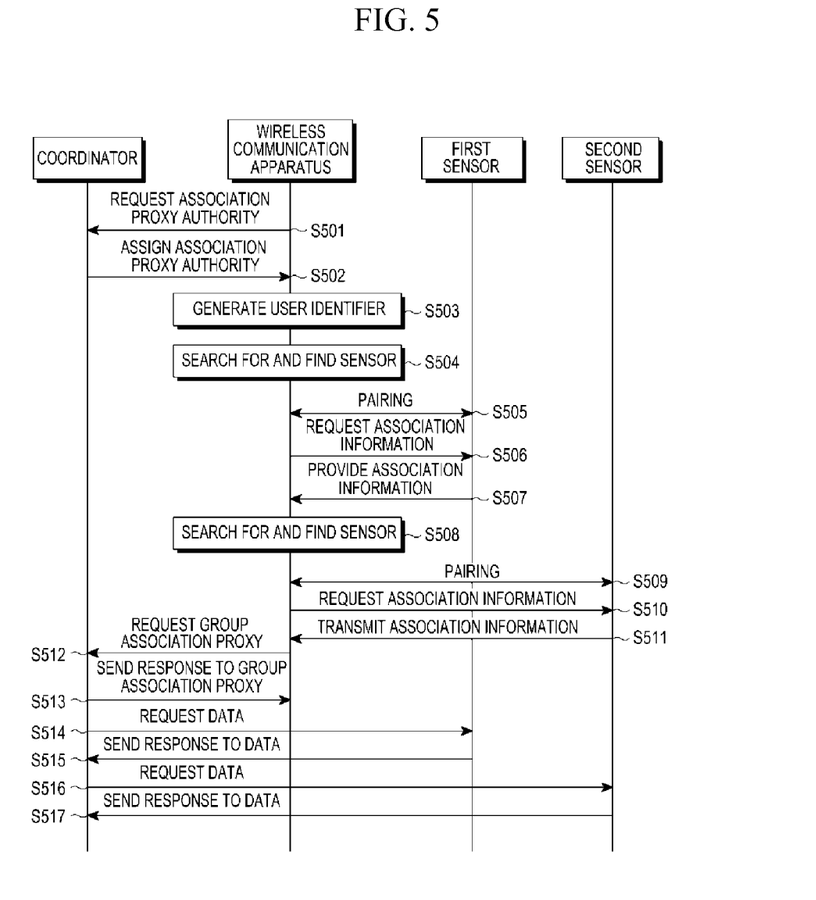
FIG. 5 is a timing diagram related to a method of controlling a communication system according to yet another embodiment of the present invention.

FIG. 5 is a timing diagram related to a method of controlling a communication system according to yet another embodiment of the present invention. The first and second sensors according to FIG. 5 do not include the storage medium for storing the user identifier in contrast with those of FIG. 3A.

Accordingly, the wireless communication apparatus of the communication system of FIG. 5 establishes pairings with the first and second sensors in steps S505 and S509 in contrast with the wireless communication apparatus of the communication system of FIG. 3A, makes the request for the association information in steps S506 and S510, receives the association information in response to the request in steps S507 and S511, and does not additionally provide the user identifier to the first and second sensors.

In step S512 of receiving the request for the group association proxy, the coordinator of the communication system according to FIG. 5 receives the user identifier, and can establish a database for an interworking between the sensor identifier list and the user identifier based on the received user identifier. Meanwhile, other steps S501 to S511 and S513 to S517 of FIG. 5 can be constructed in the same way as those of FIG. 3A, and accordingly detailed descriptions of steps S501 to S511 and S513 to S517 of FIG. 5 will be omitted herein.

Figure 6A:
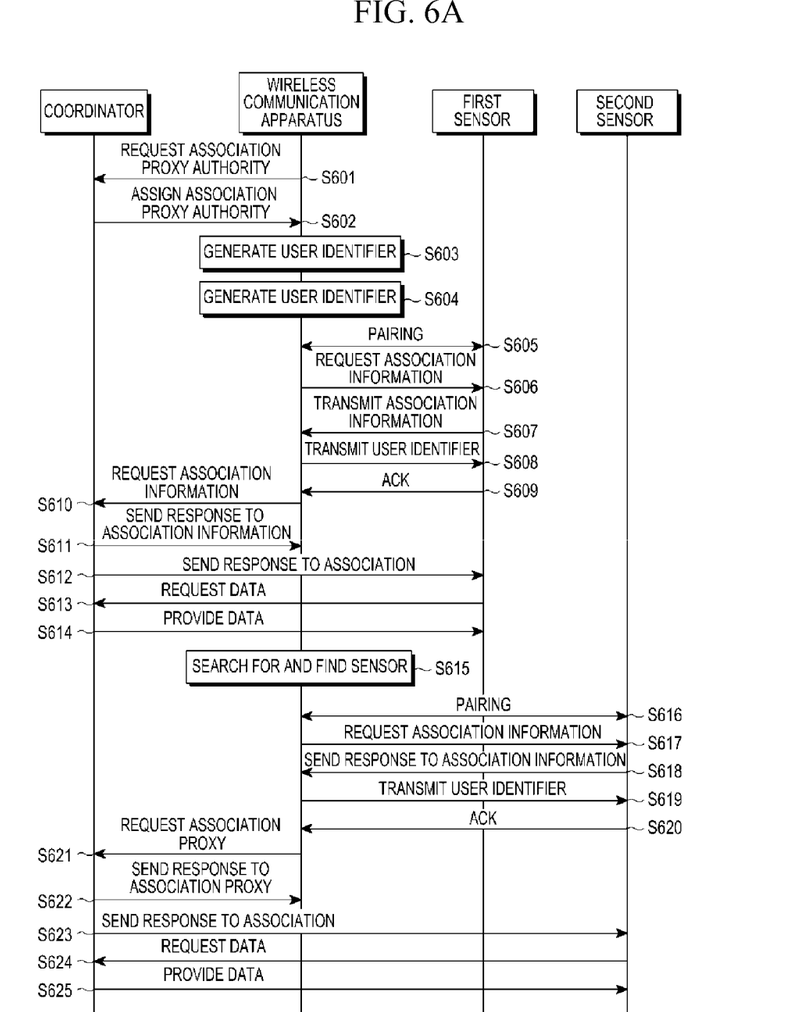
FIG. 6A is a timing diagram related to a method of controlling a communication system according to still another embodiment of the present invention.

FIG. 6A is a timing diagram related to a method of controlling a communication system according to still another embodiment of the present invention. The method of controlling the communication system according to FIG. 6A is similar to the method of controlling the communication system according to FIG. 3A. However, the method of controlling the communication system of FIG. 6A does not provide the address pool in giving the proxy authority and thus does not provide the address when the wireless communication apparatus makes the request for the association information from the first sensor. Further, right after the wireless communication apparatus stops establishing the pairing with the first sensor in step S606 and operating the association with the first sensor in steps S606 and S607, the association between the coordinator and the first sensor is established in steps S610 and S611 and thus data transmission/reception is performed between the coordinator and the first sensor in steps S613 and S614. The data transmission/reception may be performed after the pairings with the sensors are stopped. Thereafter, when data reception by the coordinator from the first sensor is stopped, the pairing between the second sensor and the wireless communication apparatus is established in step S616, and association operations in steps S617 and S618, association establishments in steps S621 and S622, and data transmission/reception in steps S624 and S625 are performed.

Meanwhile, the wireless communication apparatus according to FIG. 6A makes a request for a single association proxy instead of the group association proxy in steps S610 and S621 of making the request for the association proxy, and accordingly the association proxy may contain only information on a single sensor, that is, information on the first sensor or the second sensor, instead of the sensor information list. Further, an address used by the sensor may be included in the single association proxy response.

Figure 6B:
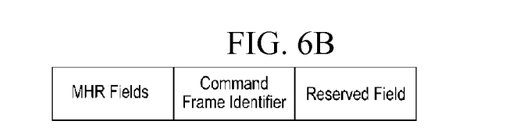
FIGS. 6B to 6C illustrate frame formats of a packet transmitted and received in the communication system of FIG. 6A.
Figure 6C:
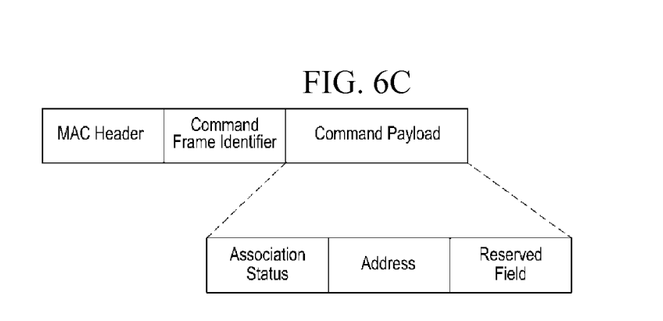

Accordingly, FIG. 6B does not include an address area in contrast with FIG. 3E, and FIG. 6C may additionally include the address area in contrast with FIG. 6C.

Figure 7:
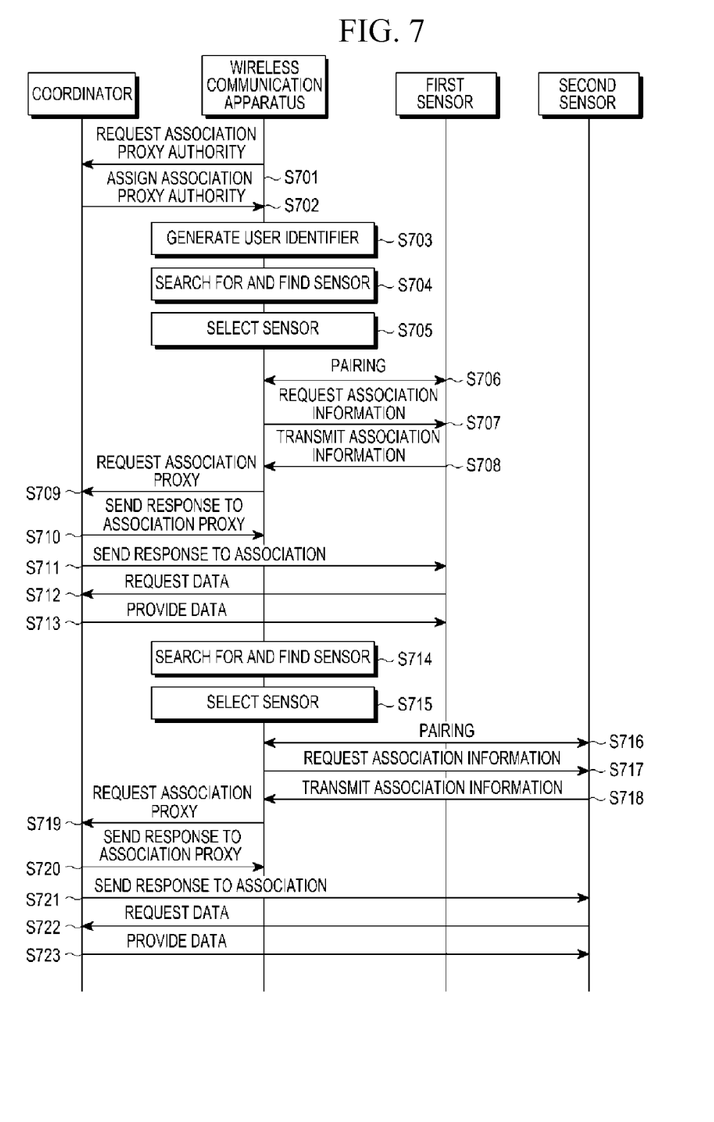
FIG. 7 is a timing diagram related to a method of controlling a communication system according to another embodiment of the present invention.

FIG. 7 is a timing diagram related to a method of controlling a communication system according to another embodiment of the present invention. The first and second sensors of the communication system according to FIG. 7 do not include the storage medium for storing the user identifier in contrast with the first and second sensors of the communication system according to FIG. 6.

Accordingly, the wireless communication apparatus of the communication system according to FIG. 7 establishes pairings with the first and second sensors in steps S706 and S716 in contrast with the wireless communication apparatus of the communication system according to FIG. 6, makes the request for the association information in steps S707 and 717, receives the association information in response to the request in steps S708 and 718, and does not additionally provide the user identifier to the first and second sensors.

In steps S709 and S719 of receiving the request for the individual association proxy, the coordinator of the communication system of FIG. 7 receives the user identifier, and can configure the database for an interworking between the sensor identifier list and the user identifier based on the received user identifier. Meanwhile, other steps of FIG. 7 can be constructed in the same way as those of FIG. 3A, and accordingly detailed descriptions of the steps of FIG. 7 will be omitted herein.

Meanwhile, in the methods of controlling the communication system according to FIGS. 6 and 7, the coordinator can transmit the address in transmitting the association response in steps S612, S622, S710, and S720 without transmitting the address used by the sensor when the wireless communication apparatus makes the request for the association information in contrast with in the method of controlling the communication system according to FIGS. 4 and 5.

Other steps (except for steps S602, S606, S612, S702, S707, and S711) of FIGS. 6 and 7 can be constructed in the same way as those of FIG. 3A, and accordingly detailed descriptions of the steps (except for steps S602, S606, S612, S702, S707, and S711) will be omitted herein.

Figure 8:
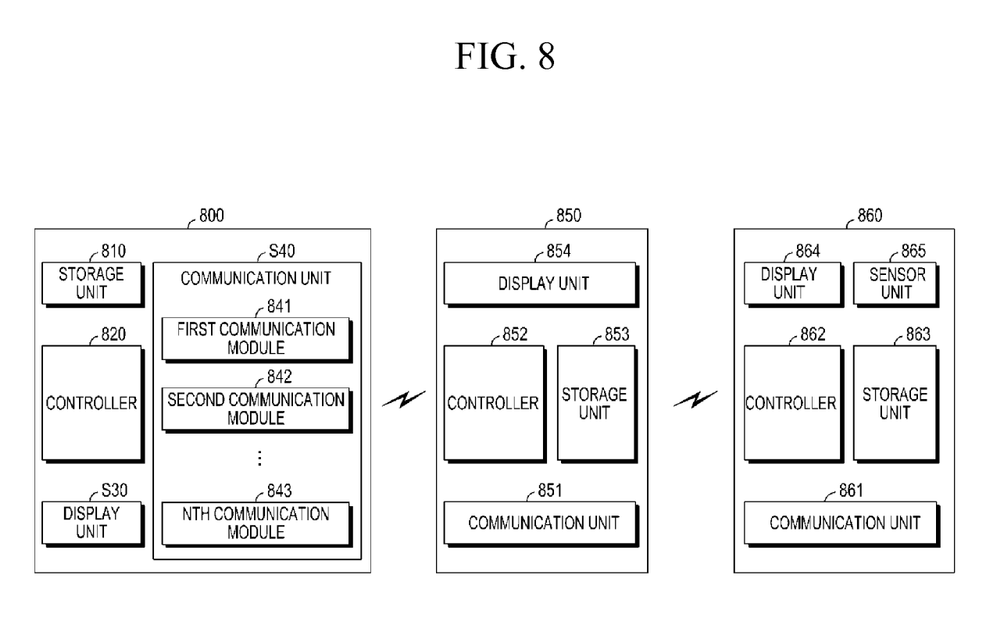
FIG. 8 is a block diagram of a communication system according embodiments of the present invention.

FIG. 8 is a block diagram of a communication system according embodiments of the present invention.

As shown in FIG. 8, a coordinator 800 includes a storage unit 810, a controller 820, a display unit 830, and a communication unit 840, and the communication unit 840 may include a first, a second, and an nth communication module 841, 842, and 843. A wireless communication apparatus 850 may include a communication unit 851, a controller 852, a storage unit 853, and a display unit 854. Meanwhile, for the convenience of description, a term "first" may be added to elements included in the coordinator 800, a term "second" may be added to elements included in the wireless communication apparatus 850, and a term "third" may be added to elements included in a sensor 860.

The first communication unit 840 can receive proxy authority request data for a proxy with at least one sensor 860 and the coordinator 800 from the wireless communication apparatus 850. Meanwhile, the first communication unit 840 can perform wireless communication with the respective communication modules 841, 842, and 843 through different communication schemes, and a detailed description of the wireless communication will be omitted since it has been described with reference to FIG. 1.

The first controller 820 can control such that the first communication unit 840 transmits the proxy authority in response to the proxy authority request data.

The storage unit 810 can store the proxy authority request data, additionally received user identifier information or sensor information, or data received from the sensor. The storage unit 810 can store a table to which at least one sensor information corresponding to each user identifier information is mapped. The storage unit 810 also can store an algorithm, a program, or an application required for an operation of the coordinator 800, and various types of parameters related to the algorithm, the program, the an application. The storage unit 810 may be implemented in a form of a RAM, a ROM, or an EEPROM.

The display unit 830 may be a means for displaying information on data processed by the controller 820 so that the manager can identify the information, and it is apparent to those in the skilled in the art that any means can be the display unit 830 if the means can output visual information.

The second communication unit 851 can receive the proxy authority.

The second controller 852 can generate the user identifier corresponding to the user, search for one or more sensors attached to the user, and control such that the second communication unit 851 establishes the pairing with the found one or more sensors.

Meanwhile, the storage unit 853 receives a proxy authorization message from the coordinator and stores the received proxy authorization message. Further, the storage unit 853 can store a plurality of generated user identifiers, an inherent identifier of the wireless communication apparatus 850, association information request data generated to be transmitted to the sensor 860 later, and store an algorithm, a program, or an application required for an operation, and various types of parameters related thereto. Also, the storage unit 853 can store a table to which information on one or more sensors corresponding to information on respective user identifiers is mapped through a synchronization with the coordinator. The storage unit 810 can be implemented in a form of a RAM, a ROM, or an EEPROM.

The display unit 854 may be a means which can display information on data processed by the controller 852 so that the manager can identify the information, and it is apparent to those in the skilled in the art that any means can be the display unit 854 if the means can output visual information.

The third communication unit 861 can receive a request for association information for an association between the coordinator 800 and the sensor 860 from the wireless communication apparatus 850.

The third controller 862 can control such that the third communication unit 861 transmits the association information to the wireless communication apparatus 850 in response to the request for the association information.

The sensor 865 can detect a vital signal output from a user's body and process the vital signal to be suitable for data transmission.

Meanwhile, the storage unit 863 can store data input from the sensor unit 865 and also store information on the user identifier received from the wireless communication apparatus 850.

Here, the second controller 852 can control such that the second communication unit 851 makes a request for an association proxy between the found one or more sensors 860 and the coordinator 800 from the coordinator 800.

The second communication unit 850 can receive the association proxy in response to the request, and the first controller 820 can control such that the first communication unit 840 makes a request for data by establishing the association with the found one or more sensors 860.

The third controller 862 can control such that the third communication unit 861 transmits the data in response to the request for the data.

Meanwhile, as described above, the sensor 860 may further include the storage unit 863 for storing one or more user identifiers and the second controller 852 can control such that the second communication unit 852 transmits the user identifiers to the found one or more sensors.

Meanwhile, the second controller 852 can generate the user identifier based on an external input for the user identifier or based on an RF signal received from an RF signal generating means disposed in the surroundings of the user.

Meanwhile, the second controller 852 can control such that the second communication unit 851 establishes the pairing based on an NFC (Near Field Communication) scheme.

Here, when communication schemes used by the found one or more sensors are equal, the second controller 852 can control such that the second communication unit 851 sequentially establishes pairings of the found one or more sensors.

As described above, the association information may contain at least one of the identifier of the sensor 860 and information on the sensor 860. The information on the sensor 860 may be one of a serial number of the sensor 860, a type of the sensor 860, and a battery type. When the coordinator 800 includes a database for the information on the sensor 860, the association information may contain only the identifier of the sensor 860. When the coordinator 860 does not include the database for the information on the sensor 860, the first controller 820 can build a database for an identifier list of the sensor 860 based on the user identifier.

Meanwhile, the second controller 852 can control such that the second communication unit 851 establishes pairings only for some sensors of the found sensors 860. Here, the second controller 852 can select some sensors based on an external input signal. Further, the second controller 852 can select some sensors based on an intensity of a signal received from the found sensors 860. For example, the second controller 852 can control such that the second communication unit 851 establishes the pairing only for sensors of which an intensity of the received signal is the same as or larger than a preset value.

The association proxy may contain at least one of the identifier of the wireless communication apparatus 850, the user identifier, and information on each of the found sensors 860.

The second controller 852 can control such that the second communication unit 852 transmits the identifier of the wireless communication apparatus 850 together with proxy authority request data.

Further, the second controller 852 can control such that the second communication unit 851 additionally transmits information on the coordinator together with the association information. In this case, the information on the coordinator 800 may be information on an address storing data received from the found one or more sensors 860.

While the invention has been shown and described with reference to certain exemplary embodiments thereof, it will be understood by those skilled in the art that various changes in form and details may be made therein without departing from the spirit and scope of the invention as defined by the appended claims. Therefore, various modifications and changes can be made to the present invention within the technical spirit and scope of the present invention, and the modifications and changes should not be separately construed from the technical spirit and scope of the present invention.

The invention claimed is:

1. A method of controlling one or more sensors and a coordinator by a wireless communication apparatus, the method comprising:
   transmitting a request for a proxy authority to a coordinator;
   receiving the proxy authority from the coordinator, in response to the request for proxy authority;
   identifying a user identifier, based on the received proxy authority;
   searching for one or more sensors based on the received proxy authority;
   establishing one or more pairings with the searched one or more sensors;
   transmitting, to the searched one or more sensors, a request for association information for associating at least one sensor among the searched one or more sensors with the coordinator;
   receiving the association information, in response to the request of association information;
   transmitting, to the coordinator, a request for a group association proxy for associating the searched one or more sensors with the coordinator, based on the identified user identifier; and
   receiving the group association proxy, in response to the request of group association proxy.

2. The method as claimed in claim 1, further comprising transmitting the user identifier to the searched one or more sensors after receiving the association information.

3. The method as claimed in claim 1, wherein the identifying of the user identifier comprises identifying the user identifier based on an external input for the user identifier.

4. The method as claimed in claim 1, wherein the identifying of the user identifier comprises identifying the user identifier based on an RF signal received from an RF signal identifying means located in surroundings of the user.

5. The method as claimed in claim 1, wherein the establishing of the one or more pairings comprises establishing the one or more pairings based on a near field communication (NFC) scheme.

6. The method as claimed in claim 1, wherein the establishing of the one or more pairings comprises sequentially establishing the one or more pairings with the searched one or more sensors when communication schemes used by the searched one or more sensors are equal.

7. The method as claimed in claim 1, wherein the association information contains at least one of an identifier of the searched one or more sensor and information on the searched one or more sensor.

8. The method as claimed in claim 7, wherein the information on the sensor is at least one of a serial number of the searched one or more sensor, a type of the searched one or more sensor, and a battery type.

9. The method as claimed in claim 7, wherein, when the coordinator includes a database for the information on the searched one or more sensor, the association information contains the identifier of the searched one or more sensor.

10. The method as claimed in claim 7, wherein, when the coordinator does not include a database for the information on the searched one or more sensor, after receiving the request for the association proxy comprises building an identifier list database of the searched one or more sensor based on the user identifier by the coordinator.

11. The method as claimed in claim 1, wherein the establishing of the one or more pairings comprises establishing the one or more pairings only with some of the searched one or more sensors.

12. The method as claimed in claim 11, wherein the some of the searched one or more sensors are selected based on an external input signal.

13. The method as claimed in claim 11, wherein the some of the searched one or more sensors are selected based on an intensity of a signal received from the searched one or more sensors.

14. The method as claimed in claim 1, wherein the association proxy contains one or more of an identifier of the wireless communication apparatus, the user identifier, and information on each of the searched one or more sensors.

15. The method as claimed in claim 1, wherein the transmitting of the request for the proxy authority comprises transmitting an identifier of the wireless communication apparatus as well by the wireless communication apparatus.

16. The method as claimed in claim 1, further comprising:
   establishing, by the coordinator, one or more associations with the searched one or more sensors using the group association proxy, by the coordinator;
   transmitting, by the coordinator, one or more requests for data to the searched one or more sensors; and
   receiving, by the coordinator, the data in response to the request for the data.

17. The method as claimed in claim 1, wherein the identifying of the user identifier comprises identifying the user identifier based on one of the received proxy authority or identified information via a wireless communication.

18. The method as claimed in claim 17, wherein the identifying of the user identifier comprises identifying the user identifier based on a radio-frequency identification (RFID) tag.

* * * * *